United States Patent
Woods et al.

(12)

(10) Patent No.: US 7,879,561 B2
(45) Date of Patent: Feb. 1, 2011

(54) DETECTION OF CHRONIC KIDNEY DISEASE PATIENTS OR CORONARY ARTERY DISEASE USING BONE MORPHOGENIC PROTEIN-4

(75) Inventors: Thomas Cooper Woods, New Orleans, LA (US); Corey Keith Goldman, Metairie, LA (US)

(73) Assignee: Ochsner Clinic Foundation, New Orleans, LA (US)

(*) Notice: Subject to any disclaimer, the term of this patent is extended or adjusted under 35 U.S.C. 154(b) by 0 days.

(21) Appl. No.: 12/422,630

(22) Filed: Apr. 13, 2009

(65) Prior Publication Data

US 2009/0246799 A1 Oct. 1, 2009

Related U.S. Application Data

(63) Continuation of application No. PCT/US2007/081259, filed on Oct. 12, 2007.

(60) Provisional application No. 60/829,445, filed on Oct. 13, 2006.

(51) Int. Cl.
*G01N 33/53* (2006.01)
*G01N 33/70* (2006.01)
*C07K 14/51* (2006.01)

(52) U.S. Cl. .......................... 435/7.1; 435/98
(58) Field of Classification Search ....................... None
See application file for complete search history.

(56) References Cited

U.S. PATENT DOCUMENTS

| 6,723,698 B2 | 4/2004 | Rueger et al. |
| 2002/0173453 A1 | 11/2002 | Akella et al. |
| 2006/0014278 A1 | 1/2006 | Khillan et al. |

OTHER PUBLICATIONS

Griethe et al. Bone morphogenic protein-4 expression in vascular lesions of calciphylaxis. J Nephrol. Sep.-Oct. 2003;16(5):728-32.*
International Search and Written Opinion report issued on May 21, 2008 by the United States Patent Office as International Search Authority on PCT/US07/81259.
International Preliminary Report on Patentability issued on Apr. 23, 2009 by the International Bureau of WIPO on PCT/US07/81259.

* cited by examiner

*Primary Examiner*—David S Romeo
(74) *Attorney, Agent, or Firm*—Jones, Walker, Waechter, Poitevent, Carrere & Denegre, L.L.P.

(57) ABSTRACT

The invention is a method of detecting CAD in a CKD diagnosed human patient or CKD in a diagnosed CAD patient, or detection the presence of both CDK and CAD by assaying a plasma or serum sample of a human patient for elevated levels of BMP-4.

13 Claims, 6 Drawing Sheets

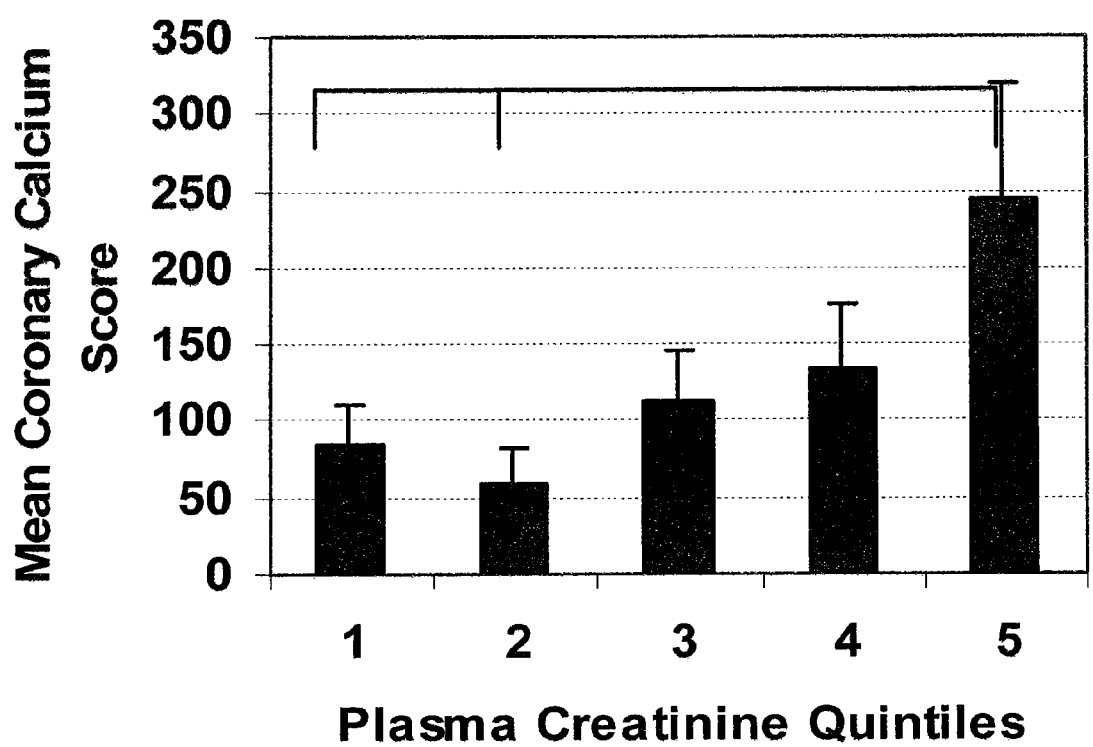
Figure 1. Coronary artery calcium scores grouped by creatinine quintiles. Brackets indicate significant differences as determined by one-way ANOVA (p<0.05).

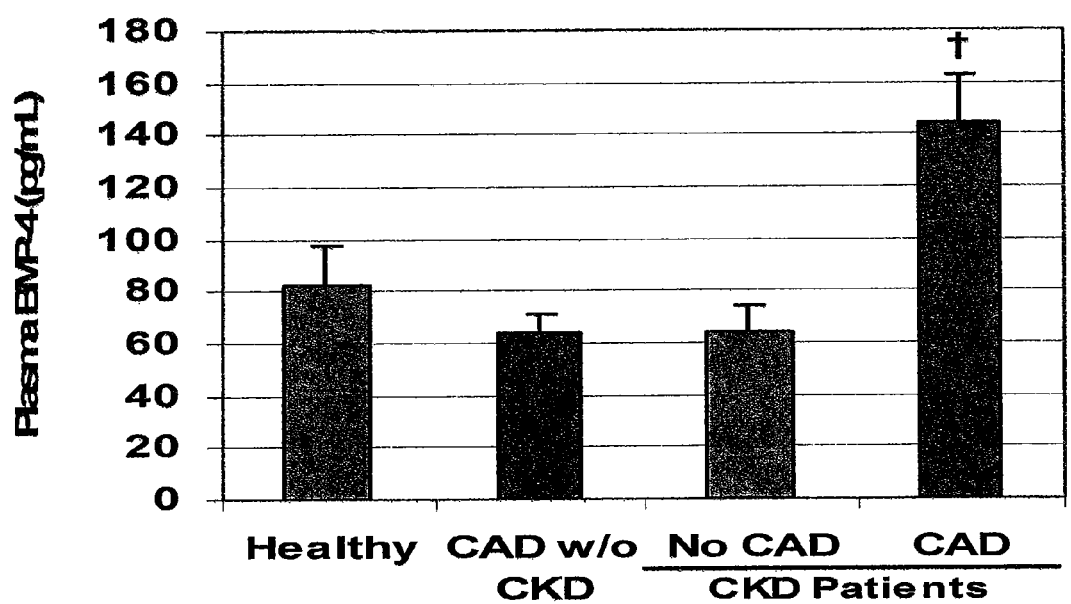
Figure 2. BMP-4 is elevated in patients with CAD and CKD. † indicate significant differences as determined by one-way ANOVA (p<0.01).

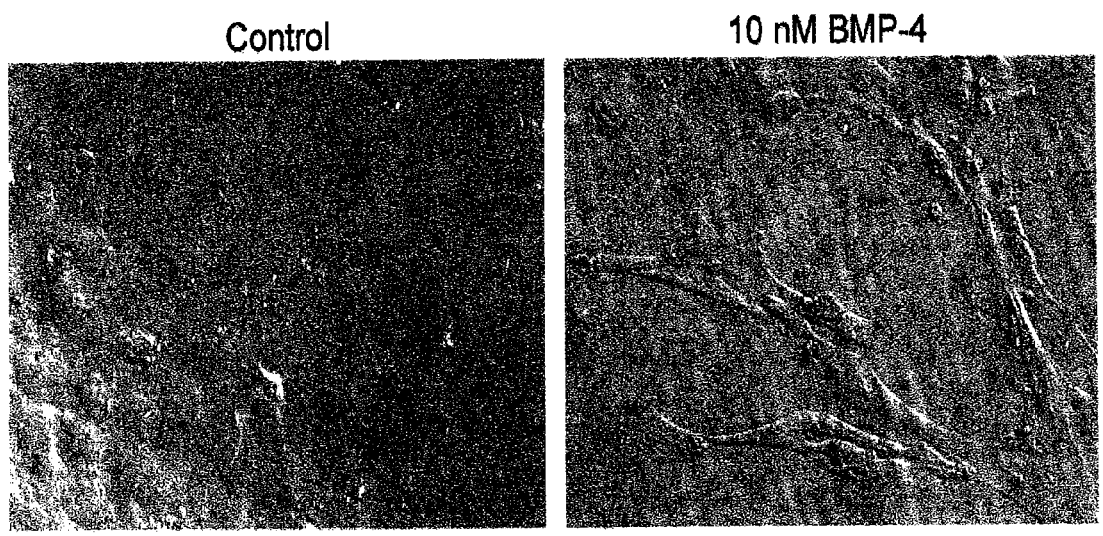
Figure 3. BMP-4 induces a morphological change in VSMCs

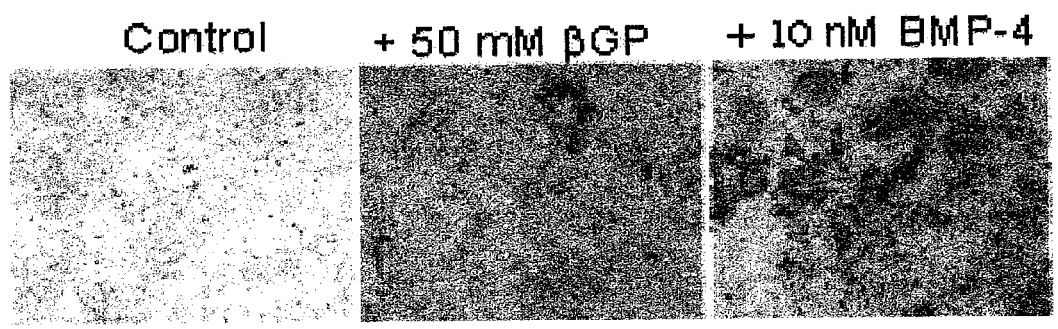
Figure 4. BMP-4 induces calcium deposition in VSMCs

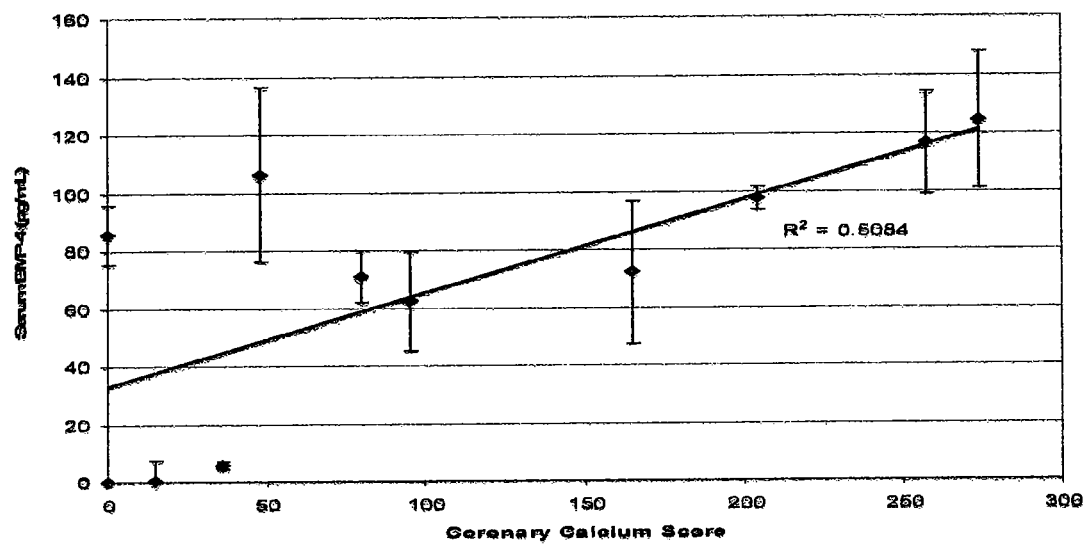
Figure 5. Serum BMP-4 levels correlate with Coronary Artery Calcification.

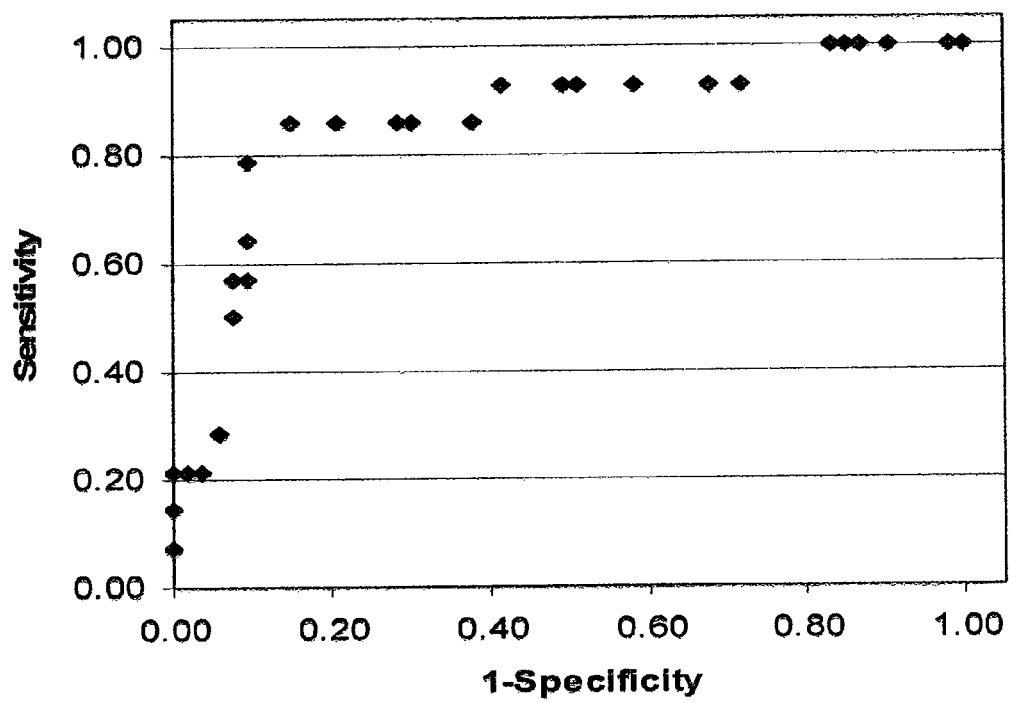
Figure 6. Receiver operator curve for the use of serum BMP-4 levels to identify patients with CAD and CKD.

DETECTION OF CHRONIC KIDNEY DISEASE PATIENTS OR CORONARY ARTERY DISEASE USING BONE MORPHOGENIC PROTEIN-4

PRIORITY CLAIM

This application is a continuation of PCT/US07/81259 filed on Oct. 12, 2007, which claimed the priority benefit under 35 U.S.C. 119(e) 2 of U.S. Provisional Application No. 60/829,445 filed on Oct. 13, 2006, and this application claims the priority benefit of these application, and hereby incorporated by reference these applications.

FIELD OF INVENTION

This invention relates to detection of Chronic Kidney Disease Patients (CKD) in patients having Coronary Artery Disease (CAD) or vice versa, or the detection of both CAD and CKD by assaying for a particular protein in serum or plasma, in particular, the bone morphogenic protein-4 (BMP-4) protein.

BACKGROUND OF INVENTION

That CKD and vascular disease are closely connected has been recognized for several years, although the nature of this connection remains unclear. Among dialysis patients, cardiovascular mortality remains the number one cause of death with rates ranging from 10 to 30 times greater than seen in the general population despite adjustments for other risk factors. In 2003, the American Heart Association released a Scientific Statement outlining the data supporting that CKD patients should be considered in the highest risk group for cardiovascular disease, recognizing the need to treat this patient population aggressively for cardiovascular risk factors. Despite the growing recognition that CKD patients are at greater risk of vascular disease, much remains to be understood as to the mechanisms behind this increased risk. This patient population has a greater prevalence of risk factors for cardiovascular disease, as defined by the Framingham study. However, cross-sectional studies have demonstrated that the Framingham Risk Equation does not adequately predict the magnitude of the increased risk of cardiovascular disease seen in CKD patients. Thus, additional risk factors may be present in CKD patients leading to the increased atherosclerosis beyond those considered most important in the general population. Recent studies suggest that the increased vascular calcification seen in dialysis patients compared with the general population may play a role in the increased risk of cardiovascular events.

Calcification is common in the coronary arteries of dialysis patients, including adolescents and young adults. In patients with known coronary artery disease, those with CKD have been shown to have 2- to 5-fold greater coronary artery calcification, as measured by electron-beam CT scan. Similarly, comparisons of coronary atherosclerotic lesions from age/gender-matched autopsy specimens showed a similar lesion size, but with greater calcification in those patients with end-stage renal disease (ESRD). These data suggest that the atherosclerosis in CKD patients may progress at a similar rate as normal patients, but with greater calcification. Increased calcification is also seen in the peripheral vasculature of CKD patients. Several studies of ESRD patients have indicated an increased stiffness in the larger arteries resulting in increases in pulse wave velocities and pulse pressures as well as mortality. Pulse wave velocities and pulse pressures have also been demonstrated to be proportional to the magnitude of calcification as detected by ultrasound. Histological studies have demonstrated an increased intimal thickness, intimal calcification, and medial calcification in the renal arteries of dialysis patients compared with age-matched autopsy specimens. Other studies have demonstrated a similar increase in the calcification of the iliac and radial arteries of dialysis patients.

Previous data from our laboratory, comparing the degree of coronary artery calcification in patients with varying plasma creatinine levels, also support these findings. Plasma creatinine levels are commonly used to assess the renal function of a patient with higher values indicating decreased function. We grouped the patients by plasma creatinine quintiles and compared the mean coronary calcium scores obtained using a Philips Mx-8000 16 detector CT scanner (FIG. 1). Our hypothesis was that CKD patients will have increased levels of proteins with osteogenic potential, such as the BMP family, in their plasma leading to an increase in the vascular calcification seen in this patient population. These data support our hypothesis by demonstrating that patients with decreased kidney function have elevated levels of coronary artery calcification. Taken together these data demonstrate that CKD patients have greater vascular calcification, and that this increase in vascular calcification may play an important role in the increased risk of CKD patients for coronary artery disease (CAD).

Diagnostic and therapeutic radiological procedures require the use of iodinated contrast media. These procedures include diagnostic catheterizations to determine the presence of vascular disease and percutaneous coronary interventions (PCI, commonly referred to as balloon angioplasty) for the treatment of CAD. A minor and temporary decrease in glomerular filtration rate, an indication of impaired renal function, is common in patients undergoing radiological procedures using iodinated contrast media. In a small percentage of the general population a more severe impairment of renal function occurs that is referred to as contrast-induced nephropathy (CIN, also known as radiocontrast nephropathy or contrast associated nephropathy). CIN is defined as an increase in absolute serum creatinine >0.05 mg/dL or in relative creatinine of >25%, and occurs in ~1.2 to 1.6% of the general population. While overall CIN rates are low, the occurrence of CIN is extremely high in certain high risk patients, including CKD patients, making it the leading cause of morbidity and mortality in this patient group following PCI. The incidence of CIN in patients with impaired renal function prior to PCI has been reported to be as high as 55%. Furthermore, several studies have demonstrated that the risk of CIN increases with an increase in serum creatinine, an indicator of CKD. Those patients that develop CIN exhibit an increase in morbidity and in both in-hospital and long-term mortality. To date no clearly effective method to prevent CIN has been found, making early identification of high risk patients coupled with careful management of the extent of their exposure to contrast media the best method to prevent CIN. The ability to identify those CKD patients with an increased risk of CAD through the measurement of BMP-4 serum levels will allow the physician to more accurately differentiate those CKD patients that require aggressive CAD treatments such as PCI from those who might forego exposure to contrast media due to a diminished risk of CAD. Currently no such clinical test exists.

Over the past ten years, it has become clear that vascular calcification occurs through a cell-mediated active process. First, the deletion of certain genes (e.g. matrix gla protein and osteoprotegrin) has been shown to increase vascular calcification in animals. Histological analysis has demonstrated the presence of several osteogenic proteins in regions of arterial calcification. This led to the hypothesis that cells in the vessel wall dedifferentiate into an osteoblast-like state, and that vascular calcification occurs through a mechanism similar to that of normal bone production. VSMCs have been shown to undergo dedifferentiation to an osteoblast-like state in vitro, and calcifying vascular cells have been isolated from primary VSMC cultures. Others have suggested that pericytes migrate from the adventia to the media and intima and differentiate into an osteoblast-like state. Finally, circulating mesenchymal stem cells may also accumulate at sites of vascular injury and differentiate into an osteoblast-like cell. Despite this debate, it is clear that cells within the calcified regions of the vasculature express proteins that are not normally found in VSMCs or fibroblasts and are associated with osteogenesis. One mechanism proposed for the induction of these proteins is the up-regulation of the bone morphogenic proteins (BMPs) at the site of vascular calcification.

SUMMARY OF THE INVENTION

The invention is a method of predicting CAD or CKD, or both, by assaying a plasma or serum for elevated levels of BMP-4 protein.

BRIEF DESCRIPTION OF THE DRAWINGS

FIG. 1 is a bar plot showing coronary artery calcium scores grouped by creatinine quintiles. Brackets indicate significant differences as determined by one-way ANOVA ($p<0.01$)

FIG. 2 is a bar plot of BMP-4 levels in patient types † indicate significant differences as determined by one-way ANOVA ($p<0.01$).

FIG. 3 is a photomicrograph (40×) of VSMC

FIG. 4 is a photomicrograph (40×) of VSMC

FIG. 5 is a X-Y scatter plot of serum BMP-4 levels versus coronary calcium score.

FIG. 6 is a graph plotting sensitivity against selectivity.

DETAILED DESCRIPTION OF THE PREFERRED EMBODIMENT

BMPs are a large family of osteoinductive growth factors that play a key role in the development of numerous tissues as well as repair of adult tissues. We focused our efforts on BMP-4, and -6, as they are present in regions of vascular calcification. BMP-4 (previously known as BMP-2B) is of particular interest as implantation of BMP-4 protein or plasmids expressing BMP-4 in the muscle of mice has been shown to produce ectopic calcification. Additionally, BMP-4 infusion in mice induces hypertension and endothelial dysfunction, suggesting a non-calcification related role for this protein in vascular disease. BMP-4 is a protein having a known structure, such as disclosed in Calcif. Tissue Int. 63 (3), 221-229 (1998), "The human bone morphogenetic protein 4 (BMP-4) gene: molecular structure and transcriptional regulation";

Shore, E. M., Xu, M., Shah, P. B., Janoff, H. B., Hahn, G. V., Deardorff, M. A., Sovinsky, L., Spinner, N. B., Zasloff, M. A., Wozney, J. M. and Kaplan, F. S. or in DNA Seq. 5 (5), 273-275 (1995); "Cloning and sequence of bone morphogenetic protein 4 (BMP-4) from a human placental cDNA library";

Oida, S., Iimura, T., Maruoka, Y., Takeda, K. and Sasaki, S.

Both references are incorporated by reference. The amino acid residue sequence for BMP-4 as disclosed in these references are identical except for the latter reference having 6 fewer amino acid residues at the beginning. BMP-4 will refer to either sequence, or any subsequence that can be used to identify BMP-4. For instance, the inventor understands that R&D Systems of Minneapolis, Minn. developed an ELISA kit for assaying BPM-4 (#DY314) using only the last 116 amino acid residues of BMP-4.

Our findings have identified elevated serum or plasma BMP-4 levels as a biomarker for patients with CKD and CAD. As an initial examination of the BMP's as possible biomarkers, we looked at whether serum levels of BMP-4 might be predictive of the presence of coronary artery disease (CAD). Using a commercially available ELISA kit (R&D Systems, Minneapolis, Minn., Catalog #DY314) we measured the levels of BMP-4 in the serum of healthy volunteers and patients being seen in the Cardiac Catheterization Laboratory at Ochsner Clinic Foundation. The data was stratified into four patient groups: healthy (n=21), CAD without CKD (n=22), CKD without CAD (n=9), and CKD with CAD (n=14). As shown in FIG. 2, there is a significant elevation of BMP-4 in the serum of patients with both CAD and CKD. No correlation between creatinine and BMP-4 plasma levels was observed. Here CKD was defined using the National Kidney Foundation's 2002 KDOQI classification of the stages of kidney disease as follows (other criteria for classifying a patient as having CKD could be used, for instance, serum or plasma creatinine levels in excess of about 1.2 mg/dl (women), or 1.4 mg/dl (men) can be an indicator, the Cockcroft-Gault equation, {GFR=(140-age)*(Wt(KG))*(0.85(if a female)/(72*creatinine level)} can be used as an indicator, Blood Urea Nitrogen levels above 20, or various urine test can also be used to indicate CKD (urine protein, microalbuminuria, creatinine clearance, kidney biopsy, kidney ultrasonic or CT scan etc.)). An estimated glomerular filtration was calculated by the simplified Modification of Diet in Renal Disease equation (MDRD): eGFR (ml/min per 1.73 m$^2$)=186×(serum creatinine (mg/dl))$^{-1.154}$×(age)$^{-0.203}$×(0.742 if female). Those patients meeting the criteria for Stage 3, 4, or 5 kidney disease (eGFR≦60, with severe kidney disease present when eGFR≦30) were assigned to one of the CKD groups (3 or 4). For the purposes of this study we defined CAD as ≧50% narrowing of a coronary artery as determined angiographically or by other methods (Again, other criteria could be used as an indicator of CAD). While serum creatinine measurements are a useful tool commonly used to determine the renal function of a patient, it is preferred that eGFR be used to assess CKD status when evaluating a patient for their risk of CIN. For this reason, we used eGFR in preparing the data presented here, however serum BMP-4 levels should be effective in determining CKD patients with CAD if serum creatinine values (e.g. a serum creatinine>1.4 mg/dl) are used to diagnose CKD instead (>1.2 mg/dl for women).

In order to assess whether BMP-4 was able to induce a phenotypic change in VSMCs, we seeded 5,000 murine VSMCs/well on an 8-well glass slide. Purity of these VSMCs was previously assessed by staining for the VSMC marker α-smooth muscle actin. The VSMCs were incubated in Dulbecco's Modified Eagle's Medium (DMEM) supplemented with 0.5% FBS and 50 μg/mL ascorbic acid and either 0 (control) or 10 nM BMP-4 (R&D Systems). VSMCs incubated in the control media will enter a contractile phenotype similar to that of VSMCs found a healthy artery wall. This phenotype is characterized by a hill and valley appearance when viewed under a light microscope. When VSMCs were incubated in control media supplemented with 10 nM of BMP-4 for 14 days, a large number of cells were observed that had lost the cobblestone appearance and switched to a morphometry similar to that of osteoblasts and fibroblasts (FIG. 3). This supports our hypothesis that BMP-4 is able to shift VSMCs out of their contractile smooth muscle phenotype toward an osteoblast-like state.

In order to assess the ability of BMP-4 to induce osteoblast-like activity in VSMCs we performed a similar study and stained the cultures for calcium deposition. VSMCs were grown in DMEM supplemented with 20% FBS and 50 µg/mL ascorbic acid (normal media). Negative control cells were treated with normal media and as a positive control we treated cells with normal media supplemented with 50 mM β-glycerophosphate. After ten days cells, the calcium deposition by the VSMCs was assessed using von Kossa staining as follows. Cells were fixed with 10% formalin in PBS for 30 min. and then washed thrice with distilled water. Then the cells were stained with fresh 5% silver nitrate for 30 min. and washed thrice with distilled water. The stain was fixed with 5% sodium thiosulfate for 2 min. and washed thrice with distilled water. The result was that areas of calcification were stained black. As shown in FIG. 4, treatment of the VSMCs with 10 nM of BMP-4 for 10 days caused a significant calcium deposition. It should be noted that fewer cells remained in the positive control well after staining, which is the reason there is less staining in the positive control section of FIG. 4. This data supports the hypothesis that increased plasma levels of BMP's will lead to an increase in vascular calcification.

We believe that the elevated serum levels of BMP-4 observed in CKD patients with CAD induces increased vascular calcification, and further, that increased levels of BMP-4 could be used as an indicator of increased coronary artery calcification. Currently, diagnosis of the presence of coronary artery calcification is undertaken using a vary laborious and expensive process, as follows:

a 3-mm nominal section thickness, ECG gating at 50% of the cardiac cycle, 120 kV, 106 mA, 0.5-second gantry rotation, and a partial scan reconstruction resulting in a temporal resolution of from 250 to 300 ms. A single scout image is taken of the chest and is used to specify the scanning region, the clavicles to the diaphragmatic hiatus. Patients are requested to hold their breath during the first 10 seconds of the acquisition and allowed to breathe quietly thereafter. Three mm axial images are reconstructed with a field of view that encompasses the heart for the first scan. Calcium scoring is performed using CT workstation specifically using the preset parameters for calcium scoring with 130 agaston cutoff. Percentile calcium scores are based on well documented normograms for age and gender. (A similar method was first described in Agatston A S, Janowitz W R, Hildner F J, Zusmer N R, Viamonte M Jr, Detrano R. Quantification of coronary artery calcium using ultrafast computed tomography. J Am Coll Cardiol. 1990; 15:827-32. hereby incorporated by reference). 2002; 90:168-73.

As can be seen, a simple predictor or indicator of coronary artery calcification would be desirable.

To determine whether elevated serum BMP-4 levels coincide with increased coronary artery calcification, we measured the levels of BMP-4 in the serum of 11 patients undergoing coronary CT scan to determine a coronary calcium score, using a commercially available ELISA kit (R&D Systems, Minneapolis, Minn., Catalog #DY314). The CT scans were performed using a Philips Mx-8000 16 detector CT scanner with prospective ECG gating at 50% of the cardiac cycle, 120 kV, 106 mA, 2.5-mm slice collimation, 0.5-second gantry rotation, and a partial scan reconstruction resulting in a temporal resolution of from 250 to 300 ms. Image processing was performed using the Extended Brilliance coronary calcium scoring software (Philips).

As shown in FIG. 5, we found that serum BMP-4 levels correlated with the coronary calcium score. This correlation suggests that BMP-4 is playing an active role in vascular calcification by contributing to the increased risk of CAD in CKD patients. This also demonstrates that serum BMP-4 may be used as a biomarker for coronary artery calcification. Serum BMP-4 levels above 60 pg/mL are indicative of a patient having a coronary artery calcification score in the upper 50th percentile of risk of CAD in the general population normalized for age and gender, and hence at risk.

In order to determine a threshold value of serum or plasma BMP-4 that would identify patients with both CKD and CAD, we calculated the sensitivity, specificity, negative predictive value (NPV), positive predictive value (PPV), and overall accuracy for a series of serum BMP-4 thresholds. Sensitivity is the percentage of patients with the targeted condition who are detected by the test, and specificity is the percentage of patients who do not have the targeted condition and correctly receive a negative test result. PPV measures the percentage of patients with a positive test result with the targeted condition (CKD+CAD). NPV measures the percentage of patients receiving a negative test result who indeed do not have the targeted condition. In order to identify candidate thresholds receiver operator curves (plots of sensitivity versus 1-specificity) were used to visualize sensitivity and specificity (FIG. 6). From these analyses, we have identified a tentative threshold of about 100-105 pg/mL of serum BMP-4 as predictive of the combination of CKD and CAD in patients. This threshold exhibits a sensitivity of 86%, a specificity of 87%, a PPV of 63%, a NPV of 96%, and an overall accuracy of 87%. Thresholds below 100 (more preferred 105) begin to introduce a large number of false positives and thresholds above 120 have a higher false negative percentage. For ruling out the combined presence of CDK+CAD, a suitable threshold is less than about 105 pg/ml (more preferred, less than about 105 pg/ml, most preferred less than about 75 pg/mL).

It is also important to note that these results are for identifying patients with CAD and CKD without prior knowledge of the patients' CKD status or even CKD status. Given that creatinine levels are usually measured as part of a patient's basic blood chemistry lab work, we have approached the use of this assay as a means of determining those CKD patients at a higher risk for CAD. The data, however, support the use of the test as a stand-alone method for the identification of these patients without prior knowledge of the CKD status.

As used herein, assaying for BMP-4 includes any test that can be correlated with levels of BMP-4 in the serum or plasma to be tested. For instance, the assay may be an antibody responsive to the presence of BMP-4 or a fragment of BMP-4, or other biomolecule that can be used to detect the presence of BMP-4, its fragments or derivatives thereof, or other test procedure, such as mass spectrogram.

The invention claimed is:

1. A method of diagnosing CAD in a CKD diagnosed human patient comprising assaying a serum or plasma sample of said CKD diagnosed human patient for BMP-4 levels, wherein said BMP-4 levels indicate the presence of CAD when said BMP-4 levels are above 100 pg/mL.

2. The method of claim 1 wherein said BMP-4 levels indicate the presence of CAD when said BMP-4 levels are above about 105 pg/mL.

3. A method of diagnosing CAD and CKD in a human patient comprising assaying a serum or plasma sample of said human patient for BMP-4 levels, wherein said BMP-4 levels indicate the presence of CAD and CKD when said BMP-4 levels are above 100 pg/mL.

4. The method of claim 3 further comprising assaying said human patient for an indicator of CKD.

5. The method of claim 4 wherein assaying for an indicator of CKD comprises assaying a serum or plasma sample of said human patient for creatinine levels.

6. The method of claim 5 wherein said method further indicates the presence of CAD and CKD if said creatinine levels are above 1.2 mg/dL for females or above 1.4 mg/dL for males.

7. The method of claim 4 wherein said indicator of CKD is an estimated glomerular filtration rate.

8. The method of claim 4 wherein said indicator of CKD is a glomerular filtration rate.

9. A method of diagnosing the absence of CAD in a CKD diagnosed human patient comprising assaying a serum or plasma sample of said CKD diagnosed human patient for BMP-4 levels, wherein said BMP-4 levels indicate the absence of CAD when said BMP-4 levels are below 100 pg/mL.

10. The method of claim 9 wherein said method indicates the absence of CAD if said BMP-4 levels are below about 75 pg/mL.

11. A method of diagnosing the absence of CAD and CKD in a human patient comprising assaying a serum or plasma sample of said human patient for BMP-4 levels, wherein said BMP-4 levels indicate the absence of CAD and CKD when said BMP-4 levels are below 100 pg/mL.

12. The method of claim 11 wherein said method indicates the absence of CAD and CKD if said BMP-4 levels are below about 75 pg/mL.

13. A method of evaluating the risk of CAD in a human patient comprising assaying a serum or plasma sample of said human patient for BMP-4 levels, wherein said BMP-4 levels indicate an increased risk of CAD if said BMP-4 levels area above about 60 pg/ml.

* * * * *